United States Patent
Stammel et al.

(10) Patent No.: US 9,068,959 B2
(45) Date of Patent: Jun. 30, 2015

(54) METHOD OF TESTING A STERILIZATION PROCESS AND STERILIZATION APPARATUS

(75) Inventors: Volker Stammel, Regensburg (DE); Patrick Engelhard, Elsendorf, DE (US); Bernd Sobiech, Regensburg (DE)

(73) Assignee: Krones AG, Neutraubling (DE)

( * ) Notice: Subject to any disclaimer, the term of this patent is extended or adjusted under 35 U.S.C. 154(b) by 196 days.

(21) Appl. No.: 12/878,997

(22) Filed: Sep. 9, 2010

(65) Prior Publication Data
US 2011/0064610 A1    Mar. 17, 2011

(30) Foreign Application Priority Data
Sep. 11, 2009    (DE) .................. 10 2009 040 979

(51) Int. Cl.
| | |
|---|---|
| *A61L 2/24* | (2006.01) |
| *G01N 31/22* | (2006.01) |
| *A61L 2/00* | (2006.01) |
| *A61L 2/04* | (2006.01) |
| *A61L 9/00* | (2006.01) |
| *A61L 11/00* | (2006.01) |
| *C23F 11/00* | (2006.01) |
| *A61L 2/18* | (2006.01) |

(52) U.S. Cl.
CPC .................... *G01N 31/226* (2013.01)

(58) Field of Classification Search
CPC .............................. A61L 2/28; G01N 31/226
USPC ......................... 422/3, 28, 30, 40, 1
See application file for complete search history.

(56) References Cited

U.S. PATENT DOCUMENTS

| | | | |
|---|---|---|---|
| 3,704,096 A | 11/1972 | Verses et al. | |
| 5,139,957 A | 8/1992 | Grack | |
| 6,779,318 B2 * | 8/2004 | Wang | 53/410 |
| 7,205,016 B2 * | 4/2007 | Garwood | 426/108 |
| 2007/0017042 A1 * | 1/2007 | Cincotta et al. | 8/643 |
| 2009/0071104 A1 | 3/2009 | Fischer | |
| 2010/0199604 A1 | 8/2010 | Fischer | |

FOREIGN PATENT DOCUMENTS

| | | |
|---|---|---|
| DE | 10 2005 012 507 A1 | 9/2006 |
| DE | 10 2006 053 193 A1 | 5/2008 |
| EP | 1 144 016 B1 | 10/2001 |

(Continued)

OTHER PUBLICATIONS

Harris et al., "Coarsening in sol-gel silica thin films", Journal of Materials Science Letters 15 (1996) 132-133.*

(Continued)

*Primary Examiner* — Regina M Yoo
(74) *Attorney, Agent, or Firm* — Novak Druce Connolly Bove + Quigg LLP

(57) ABSTRACT

A method of testing a sterilization process for a packaging member such as, for example, for containers or machines, may include the steps of acting upon at least one first region of the packaging member or of the machine with an oxidizable medium. The method further includes acting upon at least one second region of the packaging member or of the machine with an oxidizing agent. The first region and the second region overlap at least in part. The method may also include visually inspecting at least one intersection region, which has been acted upon both with the oxidizable medium and with the oxidizing agent.

16 Claims, 2 Drawing Sheets

(56) References Cited

FOREIGN PATENT DOCUMENTS

| | | | |
|---|---|---|---|
| JP | 49-46440 | B | 12/1974 |
| WO | 96/33242 | A2 | 10/1996 |
| WO | 98/52621 | A1 | 11/1998 |
| WO | 01/37886 | A1 | 5/2001 |

OTHER PUBLICATIONS

European Search Report for EP 10 17 5118, dated Dec. 7, 2010.
Chinese Office Action dated Feb. 25, 2014, issued in corresponding Chinese Application No. 201010284840.7.

* cited by examiner

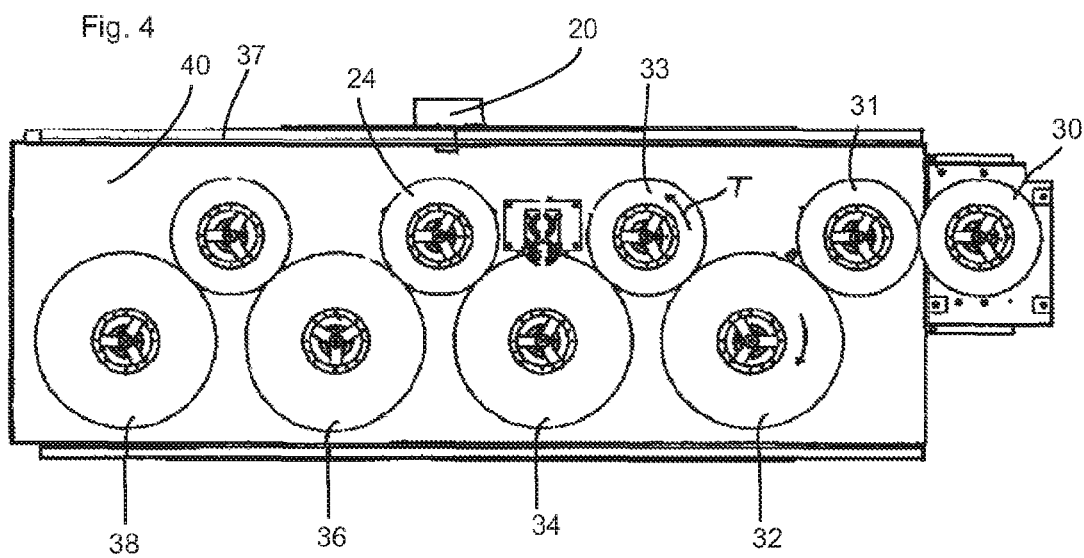
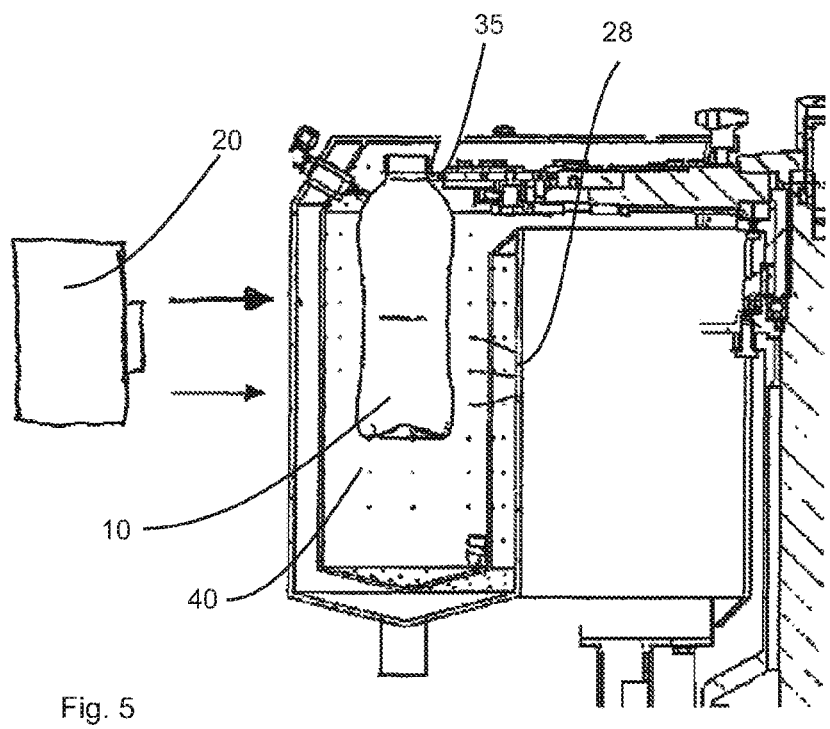

METHOD OF TESTING A STERILIZATION PROCESS AND STERILIZATION APPARATUS

CROSS-REFERENCE TO RELATED APPLICATION

This application claims the benefit of priority of German Patent Application No. 10 2009 040 979.3, filed Sep. 11, 2009, pursuant to 35 U.S.C. 119(a)-(d), the disclosure of which is incorporated herein by reference.

TECHNICAL FIELD

The present disclosure relates to a method of testing a sterilization process for packaging members and, in particular, for containers and a sterilization process for machines and, in particular, for machines for the treatment of containers, as well as to an apparatus for the sterilization of packaging members.

BACKGROUND

Conventional filling plants are used in part for filling under aseptic or hygienic conditions. In particular, in plants of this type it is necessary in part to decontaminate or to sterilize the packaging member to be filled, such as for example a plastics-material container, before the filling. The sterilization processes known in this case are for example the dry decontamination of packaging members with gaseous hydrogen peroxide ($H_2O_2$) without condensation, or also the wet decontamination of packaging members with a mixture of steam and oxidation agent such as for example peracetic acid or other oxidation agents such as for example gaseous hydrogen peroxide during condensation.

An apparatus and a method of producing plastics-material containers are described in DE 10 2006 053 193 A1. In this case at least part of the container wall is sterilized with a sterilization medium in a treatment station, in which case this sterilization medium can be a liquid and/or gaseous sterilization medium.

DE 10 2005 012 507 A1 describes a method and an apparatus for the sterile filling of liquids. In this case the containers are sterilized with $H_2O_2$, and the temperature of the containers can be set in such a way as to prevent the condensation of $H_2O_2$ on the surface of the containers.

A method and an apparatus for the sterilization of packaging means are known from EP 1 144 016 B1. In this case a liquid disinfectant and steam are supplied separately at the same time to a mixing nozzle, so that a mixture of vaporized and/or evaporated disinfectant and steam is formed by the mixing nozzle.

The subjects of DE 10 2006 053 193 A1, DE 10 2005 012 507 A1 and EP 1 144 016 B1 are thus made by reference into the subject matter of the present application in their entire scope. Furthermore, it is pointed out that, in addition to the concept of the sterilization device or the sterilization, the concepts of a disinfection device and disinfection are also applied in part.

The packaging means can be for example packaging means in the form of hollow bodies, such as pre-forms, bottles, cartons, cups, closures and the like. Furthermore, the packaging means can also be strips of packaging materials, such as for example cartons, sheets of plastics material, aluminium foils and the like.

Methods such as the roller-bottle method or CR (count reduction) tests are already known from the prior art for testing sterilization processes of this type. In these methods it is usual for the effect of the sterilization means, for example hydrogen peroxide, to be tested in a sterilization chamber. These methods, however, are relatively awkward in terms of processing and handling.

Furthermore, in these methods very many manual activities which can only be performed by a user are necessary. Furthermore, methods of this type permit a quantitative and possibly also a qualitative method, but usually it is possible with an increased outlay to test the exact, critical points on the packaging means, such as for example a base region of a plastics-material container or corrugated or grooved regions. Furthermore, in particular, microbiological tests are sensitive to external influences and, in addition, these tests require a considerable amount of time.

It may be desirable to simplify the testing of a sterilization process for packaging members, such as, for example, containers and/or machines, for example, machines for the treatment of containers.

SUMMARY

According to various aspects of the disclosure, a method of testing a disinfection process for a packaging member, such as for example, a container and/or a machine, may include a first method step of acting upon at least one first region of the packaging member with an oxidizable medium. In a further method step, at least one second region of the packaging member is acted upon with an oxidizing agent, in which case the first region of the packaging member and the second region of the packaging member overlap at least in part. In a further method step, a visual inspection of at least one intersection region, which has been acted upon both with the oxidizable medium and with the oxidizing agent, is carried out.

It may be preferable for a chemical reaction to occur between the oxidizable medium and the oxidizing agent. The effects of this chemical reaction may be advantageously (in particular visually) perceptible. The oxidizing agent may advantageously also be a sterilization agent which is used for the sterilization of the containers or the machines or machine parts, so that the action with the sterilization agent can be directly tested.

Whereas in the case of the methods known from the prior art an indirect test is carried out as to whether a sterilization agent is present in a specified region, for example in a sterilization chamber, in the case of the method proposed here a test is carried out as to whether the sterilization medium has in fact been applied to the packaging member or the machine. It is thus proposed here that the proof of an oxidative reaction is carried out in critical zones and a positive proof of the treatment in or on a packaging member by a specified chemical reaction, for example decolouration of potassium permanganate ($KMnO_4$).

One possible advantage of this method is that it is capable of being automated and it permits the possibility of a weak-point analysis with a strongly contoured container design. Furthermore, the method is capable of being carried out quickly and is also capable of being evaluated in a simple and automatic manner.

It may be desirable for the regions specified to be inner walls of the container. In this way it is possible, for example, for the first region to be acted upon in such a way that the oxidizable medium is applied to the surface or to part of the surface of the material to be investigated. This application can be carried out for example by allowing a solution to act. In this way it is possible, for example, for a potassium permanganate solution to act upon the material, and this can be carried out in an acid medium, i.e. by the addition of an acid, in particular by the addition of $H^+$ ions.

In an exemplary method between the action of the oxidizable medium upon the packaging member, such as for example a container or a region of a packaging machine, and the action of the oxidizing agent upon the packaging member there is a pre-set period of time in which the oxidizable medium acts upon the surfaces. For this purpose it is possible, for example, for the packaging member to be stored over a pre-set period of time, in which case this storage can also be carried out in some aspects with the exclusion of light. It may be advantageous for the pre-set period of time to be longer than 10 minutes, and in some cases longer than an hour, and in some cases longer than a day, and in some cases longer than two days. It is also possible, however, for the periods of time specified to be altered significantly in a manner dependent upon the reaction conditions.

In an exemplary method the oxidizable medium is selected from a group of media which includes potassium permanganate, fuchsine, combinations thereof or the like. In particular, it is possible for the oxidizable medium specified to be oxidized by the oxidizing agent which is to be applied subsequently and which in particular is also the sterilization medium used in the working operation.

In an exemplary method the packaging member is acted upon with the oxidizing agent in a manner adapted to the working operation of a plant for the sterilization of containers. As mentioned above, the methods are used for testing a sterilization procedure. In this sterilization procedure the packaging member is acted upon in a pre-determined manner with the sterilization medium. For the test operation it may be advantageous for the packaging member to be acted upon in the same manner with the sterilization medium which also represents the oxidizing agent in order to allow the plant to be tested under operating conditions in this way.

It may be desirable for the oxidizing agent to be a gaseous oxidizing agent, and the container to be sterilized may be advantageously acted upon with this oxidizing agent for a pre-set period of time. In this case the physical parameters of this action such as temperature, pressure, concentration, time of action and the like may be advantageously capable of being set.

In an exemplary method the packaging member is filled with the oxidizable medium. In this way it is possible for example for a potassium permanganate solution to be poured into the container in order to act upon the inner wall of the containers. It would also be possible, however, for the container to be immersed in a potassium permanganate bath, for example in order to act upon an outer wall of said container.

It may be advantageous for the oxidizable medium to be removed again from the packaging member, in which case this removal is carried out in particular before the packaging member is acted upon with the oxidizing agent. In this way it is possible for example for an excess of a specified solution such as a potassium permanganate solution to be removed. It may then be advantageous for the container to be dried or for the resulting layer to be surface-dried. In an exemplary method it is also possible to moisten the layer, for example with water or with an acid medium, in order to improve the subsequent reaction.

In an exemplary method the filling takes place in an acid environment, for example at a pH value of approximately 4. It would also be possible, however, for the filling to take place under non-acid conditions. In addition, it would be possible for the container not to be dried, in particular after the action of the oxidizing medium. Drying the treated surface may be advantageous, in particular for the dry sterilization method and, in particular for the sterilization method using $H_2O_2$ without condensation. In some aspects, the visual inspection of the intersection region is carried out in such a way that the occurrence of decolouration of the oxidizable medium is observed. In this case in particular a visual detection of a decolouration occurring in this way may be advantageous. It would also be possible, however, for photometric methods or even cameras to be used for the detection. In this case it would be possible for example for the container to be turned on a stationary camera and to be observed by it or even for a plurality of cameras to be provided.

It may be advantageous for the oxidizing agent to be selected from a group of oxidizing agents which contains $H_2O_2$, peracetic acid, chlorine dioxide, ozone, combinations thereof and the like. In this way it is also possible for a suitably prepared container or a container treated with the oxidizable medium to be introduced into a machine inlet of a sterilization apparatus, so that it is treated in the same way as the other containers. This container can be removed again at the outlet and the efficiency of the sterilization process can be assessed.

In this way, an oxidizable indicator is generally changed in colour by contact with a disinfectant with an oxidative effect, so that the oxidation results in a recognizable change in colour, for example from violet to colourless. The oxidative effect of the disinfection method upon a packaging member or a machine/surface of a plant is proved by this colour reaction, in which the sterilization agent can be inter alia hydrogen peroxide. The detection reaction by a change in colour is a known method according to the chemical formula:

$$5H_2O_2 + 2\,KMnO_4 + 3H_2SO_4 \rightarrow 2MnSO_4 + K_2SO_4 + 8H_2O + 5O_2$$

The potassium permanganate may thus be advantageously mixed with an $H^+$ ion supplier, for example any desired acid, such as sulphuric acid in the example above, and is then applied to the packaging member for a defined time (for example 4 days), in particular under room conditions. It may be advantageous for the packaging member to be subsequently stored under room conditions (for example at a temperature of 20° C. and with an air moisture of 50%, and it may be advantageously protected from light).

During this time a brownish violet colour film is formed on the surface of the packaging member being treated, or, if the detection is to be carried out in a machine, in a region of the machine. It is therefore stated that the present method can be used not only for testing a sterilization process of packaging member, but also for testing a sterilization process of parts of a plant and, in particular, parts of a plant which are component parts of a plant for the treatment of containers. Such a plant can be selected from a group of plants which includes labelling machines, filling machines, sterilization plants for containers, conveying devices, closure units for containers, blow-moulding machines and the like.

The precipitate specified can also be formed without an $H^+$ ion source, but the colour reaction is intensified by the addition of an acid. Commercially available chemicals may advantageously be used for the preparation. In this case the packaging member can, as mentioned above, be both hollow bodies such as plastics-material pre-forms of PET, closures, cups as well as already produced bottles and cardboard packages and packaging material, and strips of packaging material and aluminium foils for sealing package openings.

Furthermore, the proof of the reaction of an oxidizing agent on plants or machine surfaces can be detected with the method, such as for example in the case of a spray-marking test for surface-cleaning systems.

In this way, the method according to the disclosure is used for visualizing a decontamination or sterilization process which is not visually detectable at present (dry, non-condensing decontamination) by means of gaseous $H_2O_2$. In addition, the method may likewise be suitable for visualizing the effectiveness of a wet oxidizing agent on surfaces, such as for example the application of sprayed, wet decontamination agent, such as for example peracetic acid or $H_2O_2$, as well as condensing decontamination agents such as for example $H_2O_2$ gas on surfaces.

Possible fields of application are therefore inter alia the visualization of the reaction of decontamination methods or media with an oxidative effect upon the surfaces of packaging member, as well as the above-mentioned plastics-material pre-forms, plastics-material bottles, plastics-material cups, bags with coated surfaces (such as for example plastics-material polymer coatings and aluminium coatings) or cardboard packages with coated surfaces of the type mentioned above. In addition, other possible fields of application are foils or foils with coated surfaces, for example plastics-material polymer coatings, aluminium coatings or the above-mentioned machine or plant surfaces (for example of filling machines or laboratory fixtures).

The method according to the disclosure can additionally be used to control process runs such as for example changing strips of packaging member or stop-start mechanisms in process technology plants. In this way, for example, an OK signal for the effectiveness of employed sterilization methods of packaging members can be emitted at the start of production. In addition, the reaction of decontamination methods or media with an oxidative effect can be tested during running production, by test bottles for example being inserted into a plant already running in order to establish the effectiveness of the method or a sterilization agent. In this case it is preferable to use a superordinated process-control device with which the test bottles are tracked through the entire treatment process and for example are automatically separated out at the end of the process.

Furthermore, the method can be used as an auxiliary means for testing microbiological sensitive processes in the context of starting up operation or qualification and or re-qualification processes.

The present disclosure further relates to an apparatus for the sterilization of a packaging member and, in particular, of containers or of parts of a plant. The apparatus may include a conveying device which conveys the containers along a pre-set conveying path, and a sterilization device which acts upon pre-set second regions of the containers or of the apparatus itself with a sterilizing oxidizing agent. According to the disclosure, an application device, which acts with an oxidizable medium upon pre-set first regions of the containers or of the apparatus which intersect at least in part with the pre-set second regions, is provided upstream with respect to the sterilization device.

It may be advantageous for the oxidizing agent also to be the sterilization medium which is used for the sterilization of the containers.

This application device is, in particular, an application device which acts upon the containers with a liquid medium. It may be desirable for the application device to be a filling device which pours the oxidizable medium into said containers.

In an exemplary embodiment the apparatus has an inspection device which optically inspects at least those areas which have been acted upon both with the oxidizable medium and with the oxidizing agent. In some aspects, this is an inspection device which detects colour changes of the region acted upon. This can be an inspection device for example which illuminates the containers and records an image of these containers, in which case changes in the colour of these images are established.

In an exemplary embodiment the apparatus has a removal device which is arranged downstream with respect to the application device in the conveying direction of the packaging member and which removes the oxidizable medium from the packaging member.

Furthermore, it may be advantageous for the apparatus to have a drying device for drying the packaging member, this drying device being arranged between the application device and the sterilization device in the conveying direction of the packaging member.

In an exemplary embodiment the apparatus has a conveying device which conveys the packaging member from the application device to the sterilization device. This may be for example transfer stars, conveying chains or the like.

It may be advantageous for the conveying unit to be designed in such a way that the contact time of the oxidizing medium is capable of being adapted to the packaging member. In this way it would be possible for example for a special test bottle which has been treated with the oxidizable medium to be left in said conveying unit for a pre-set time, for example 12 hours, so that the oxidizable medium is given the opportunity of acting upon the container.

Some further advantages and embodiments may become evident from the attached drawings in which the sterilization apparatus, method of sterilizing packaging members, and method of testing a sterilization process are illustrated by way of example. In this case the components of the sterilization apparatus and method, which in the figures correspond at least substantially in terms of their function, can be designated with the same reference numbers, it being unnecessary for these components to be numbered or explained in all the figures.

BRIEF DESCRIPTION OF THE DRAWINGS

In the drawings:

FIG. 4 is an illustration of an apparatus for the sterilization of containers, and FIG. 5 is an illustration of an inspection unit for an apparatus according to the invention.

DETAILED DESCRIPTION

Figure 1:
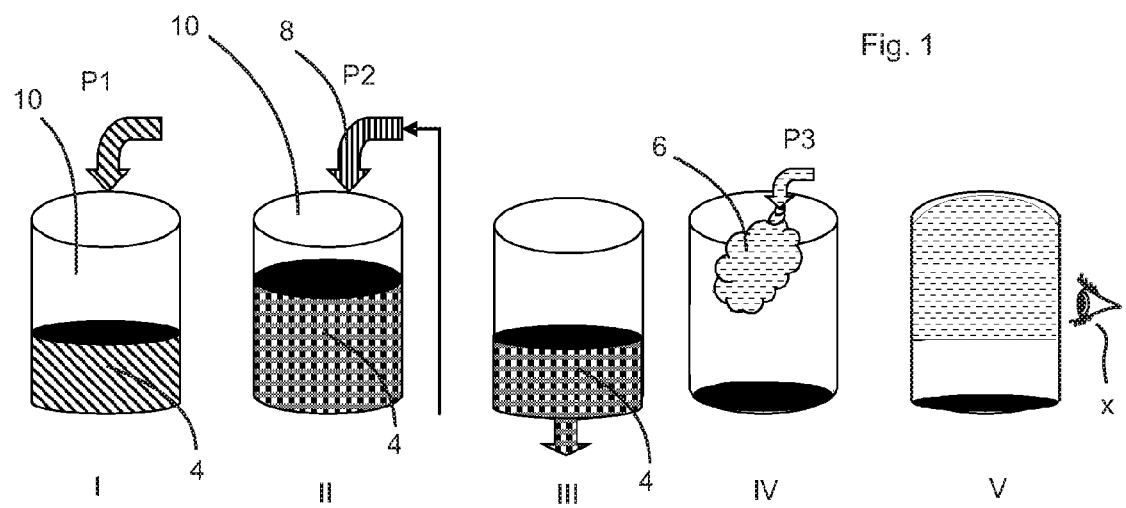
FIG. 1 is an illustration to explain a possible method flow.

FIG. 1 illustrates a possible method flow according to the disclosure. In this case a packaging member 10, such as for example a container, is filled in a first method step I with an oxidizable indicator, in this case a potassium permanganate solution, as indicated by the arrow P1. The solution itself is designated in this case with the reference number 4. After the filling, the container filled with the oxidizable medium 4 is stored for a pre-set time, for example for a time of 4 days (method step II). An acid 8 (arrow P2) can optionally also be added, such as for example $H_2SO_4$, in order to strengthen the reaction.

In a further method step III the container is emptied again, after the oxidizable medium 4 has been precipitated on the inner wall of the container in the form of a layer. The container 10 can also optionally be dried in the method step III. In this case the layer has a violet colouring. An oxidizing agent 6 is added (arrow P3) in a method step IV, the oxidizing agent in this case being gaseous $H_2O_2$. In this case this oxidizing agent can be added for example in a concentration of 3500 ppm and for example at temperatures in the region of from 60° to 100°, and in some aspects from 75° to 85°.

After the addition (step V) a decolouration occurs as a result of the contact of the oxidizing agent with the oxidizable medium, i.e. the layer which had a violet colouring until now will become colourless. By visual inspection of the container 10 it is possible to check the regions in which the oxidizing agent comes into contact with the container or for example the inner wall thereof, since it is only in these regions or in particular in these regions that the change in colour described occurs. In this way a check can be made in particular as to whether spatially critical points, for example in the base or shoulder region or possible grooves in the container, are likewise disinfected in a satisfactory manner. In method step IV the oxidizing agent is added in particular in such a way that it reaches the drinks containers even in working operation. The inspection (reference number X) of the container in method step V can also be carried out automatically, and it would be additionally possible in a reaction to such an inspection result to modify the supply of the disinfectant so that all the regions of the container are acted upon with the oxidizing agent.

The drying of the containers 10 in method step III, as described, leads to an improved formation of film on the inner surface. In order to detect the oxidative effect the surface can be moistened again so that the reaction can take place in an improved manner. The use of the decontamination method with an oxidative effect (an $H_2O_2$/air mixture is involved in this case) results in a reaction with the potassium permanganate and, as explained above, in a decolouration which can be detected visually. It is possible for photometric methods, such as visual observation, or other methods operating visually, such as for example camera systems, to be used for this visual detection.

It is pointed out that the method described in this case can also run completely automatically, i.e. in the context of a test operation for example the oxidizable medium is supplied, then the oxidizing agent which is also the sterilization agent, and in a further method step a visual inspection of the containers is carried out.

It is further possible for the method to be used in a laboratory operation in order to test a new bottle design for aseptic applications.

Figure 2:
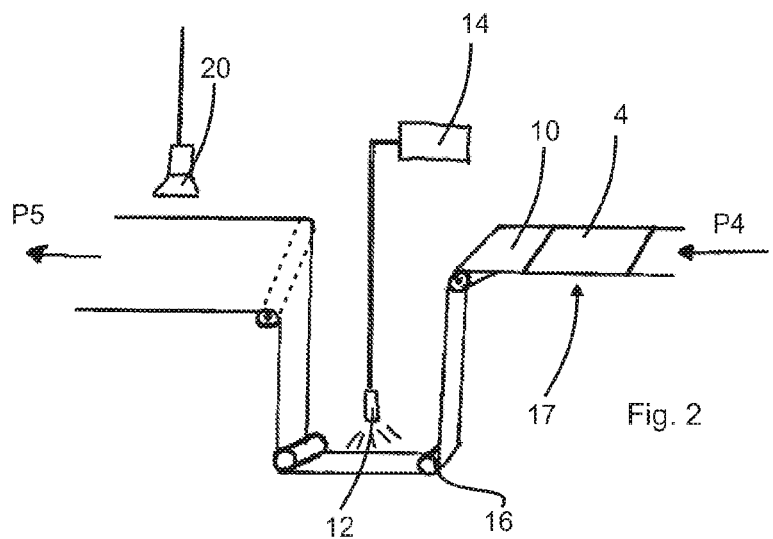
FIG. 2 shows a possible embodiment of an apparatus according to the invention.

FIG. 2 shows a possible embodiment of an apparatus according to the disclosure which is used in particular for strips of packaging material. In this case a packaging member 10 in the form of a strip of packaging material is conveyed along the arrows P4 and P5. A plurality of rolls 16 are used in this case to convey the packaging member. The reference number 17 in this case designates a region in which the oxidizable medium has been applied. The reference number 12 designates a spray head or a nozzle with which, starting from a reservoir 14, the oxidizing agent 6 is applied to the packaging member 10 or the strip of packaging material. The reference number 20 designates an optical inspection unit which checks whether the decolouration mentioned above occurs in the regions which have been acted upon both with the oxidizable medium 4 and with the oxidizing agent 6. This apparatus can have attached to it a packing machine for example (on the left in FIG. 2).

Figure 3:
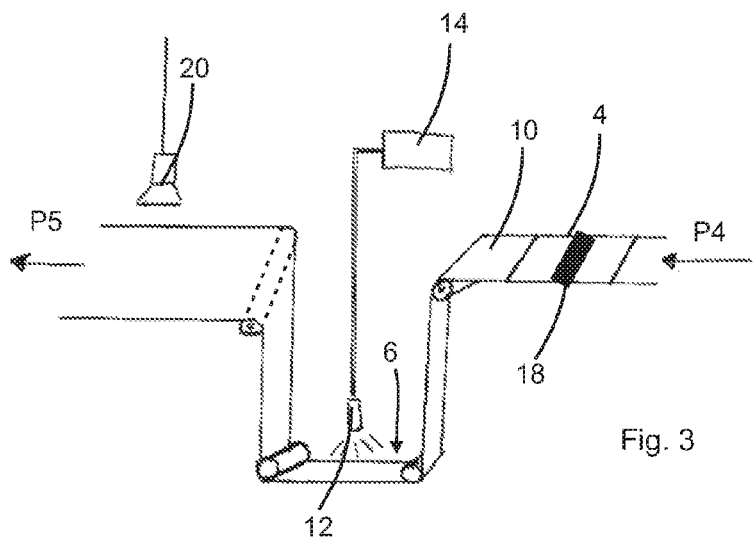
FIG. 3 is an illustration of a further embodiment of an apparatus according to the invention.

FIG. 3 shows a modification of the apparatus shown in FIG. 2. In this case the method is used for checking an adhesion point 18 between two rolls or two strips (i.e., a region of a packaging machine). Here an oxidizable medium 4 is applied to the region, and then the oxidizing agent 6 is also applied again. In this way the position of an adhesion point of this type can be precisely marked by the change in colour mentioned or the colour marking.

FIG. 4 shows a further example of an apparatus for the sterilization of containers. In this case this apparatus has a plurality of conveying units 32, 34, 36 and 38, which jointly with transfer stars convey the containers along a conveying path T. The reference number 30 designates an inlet star. In the region of the conveying unit 32 a pre-heating of the containers takes place, in the region of the conveying unit 34 a sterilization process with a sterilization device (not shown), for example by action with the oxidizing agent or sterilization medium, in the region of the conveying wheel or the conveying unit 36 a blowing-out of the containers can take place, and in a region of the conveying wheel or the conveying unit 38 a possible inspection of the containers themselves or even a further blowing-out.

The reference numbers 31, 33 and 37 designate conveying devices such as for example transfer stars or the like by which the containers are conveyed between the individual conveying units 32, 34, 36 and 38.

By means of an inspection device 20, such as for example a camera, it is possible for an investigation in the manner described above, into whether a change in colour of the oxidizable medium has taken place, to be carried out in a region downstream of the conveying wheel or the conveying unit 34. For this purpose a prepared container (cf. step III in FIG. 1) can be supplied to the plant and can be treated in the same manner as a container in normal working operation. In this case the inspection device 20 carries out an optical check as to whether a change in colour has occurred.

FIG. 5 is a detailed illustration of an inspection in this manner. In this case the container 10 is conveyed through the sterilization chamber 40 with the aid of the conveying wheel 24 or a gripping element 35 and is observed by the inspection device 20 during this transportation. It may also be advantageous for a light source 28 to be provided which illuminates the container 10 from behind, so as to simplify the observation of the containers 10 in this way.

It will be apparent to those skilled in the art that various modifications and variations can be made to the sterilization apparatus and method of testing a sterilization process of the present disclosure without departing from the scope of the invention. Throughout the disclosure, use of the terms "a," "an," and "the" may include one or more of the elements to which they refer. Other embodiments of the invention will be apparent to those skilled in the art from consideration of the specification and practice of the invention disclosed herein. It is intended that the specification and examples be considered as exemplary only.

What is claimed is:

1. A method of testing a sterilization process for a packaging member, the method comprising:
   directing an oxidizable medium to a surface of said packaging member;
   allowing a film of the oxidizable medium to form on said surface;
   directing an oxidizing agent to at least a portion of said surface with said film, contact of the oxidizing agent with the film of the oxidizable medium causing a change in the film; and
   visually inspecting a selected region of said surface of said packaging member to determine if said selected portion has been acted upon with the oxidizing agent, wherein said at least one packaging member is filled with the oxidizable medium.

2. The method according to claim 1, wherein the at least one packaging member comprises a container or a region of a packaging machine.

3. The method according to claim 1, wherein said allowing the film to form comprises waiting a period of time between said directing of the oxidizable medium and said directing of the oxidizing agent such that the oxidizable medium precipates on said surface of said packing member.

4. The method according to claim 1, wherein the film has a color, and said change in the film is decolouration.

5. A method of testing a sterilization process for at least one packaging member, the method comprising the steps of:
   acting upon at least one first region of said at least one packaging member with an oxidizable medium;
   allowing a film of the oxidizable medium to form on said at least one first region;
   acting upon at least one second region of said at least one packaging member with an oxidizing agent, said at least one first region and said at least one second region overlapping at least in part, contact of the oxidizing agent with the oxidizable medium causing a change in the film; and
   visually inspecting a selected portion of said at least one first region of said at least one packaging member to determine if said selected portion has been acted upon with the oxidizing agent, wherein the at least one packaging member is a container, and the at least one first and second regions are regions of a wall of the container and wherein the at least one packaging member is filled with the oxidizable medium.

6. The method according to claim 5, wherein between the action of the oxidizable medium upon said at least one packaging member and the action of the oxidizing agent upon said at least one packaging member there is a pre-set period of time in which the oxidizable medium acts upon the at least one packaging member.

7. The method according to claim 6, wherein the pre-set period of time is longer than 10 minutes.

8. The method according to claim 7, wherein the pre-set period of time is longer than 1 hour.

9. The method according to claim 8, wherein the pre-set period of time is longer than a day.

10. The method according to claim 5, wherein the oxidizable medium is selected from a group of media which includes potassium permanganate (KMnO4), fuchsine, and combinations thereof.

11. The method according to claim 5, wherein said at least one packaging member is acted upon with the oxidizing agent in a manner adapted to the working operation of a plant for the sterilization of containers.

12. The method according to claim 5, wherein the oxidizable medium is removed from said at least one packaging member.

13. The method according to claim 5, wherein the film has a color, and said change in the film is decolouration.

14. The method, according to one of claims 5, 6-11, or 13, of testing the sterilization process for at least one packaging member, the method comprising:
   acting upon the at least one first region of the at least one packaging member with the oxidizable medium;
   acting upon the at least one second region of the at least one packaging member with the oxidizing agent, wherein the at least one first region and the at least one second region overlap at least in part; and
   visually inspecting at least one intersection region, which has been acted upon both with the oxidizable medium and with the oxidizing agent,
   wherein between the action of the oxidizable medium upon the at least one packaging member and the action of the oxidizing agent upon the at least one packaging member there is a pre-set period of time in which the oxidizable medium acts upon the at least one packaging member, wherein the pre-set period of time is longer than 10 minutes.

15. The method according to claim 14, wherein the pre-set period of time is longer than 1 hour.

16. The method according to claim 15, wherein the pre-set period of time is longer than a day.

* * * * *